(12) United States Patent
Hall et al.

(10) Patent No.: US 8,670,828 B2
(45) Date of Patent: Mar. 11, 2014

(54) METHOD AND DEVICES FOR COUPLING A LEAD CONDUCTOR MEMBER TO A FUNCTIONAL COMPONENT

(75) Inventors: Peter Hall, Andover, MN (US); Kenneth L. Gunter, Maple Grove, MN (US); Haiping Shao, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 686 days.

(21) Appl. No.: 12/786,167

(22) Filed: May 24, 2010

(65) Prior Publication Data

US 2010/0305670 A1 Dec. 2, 2010

Related U.S. Application Data

(60) Provisional application No. 61/181,172, filed on May 26, 2009.

(51) Int. Cl.
*A61N 1/08* (2006.01)

(52) U.S. Cl.
USPC .............................. 607/37; 607/115; 607/116

(58) Field of Classification Search
USPC ............................................ 607/37, 115, 116
See application file for complete search history.

(56) References Cited

U.S. PATENT DOCUMENTS

| 4,566,467 | A | 1/1986 | DeHaan |
| 4,922,607 | A | 5/1990 | Doan et al. |
| 4,934,366 | A | 6/1990 | Truex et al. |
| 4,966,564 | A | 10/1990 | Foote |
| 5,007,435 | A | 4/1991 | Doan et al. |
| 5,385,578 | A | 1/1995 | Bush et al. |
| 5,488,768 | A | 2/1996 | Mar |
| 5,522,872 | A | 6/1996 | Hoff |
| 5,676,694 | A | 10/1997 | Boser et al. |
| 5,869,804 | A | 2/1999 | Mueller et al. |
| 6,181,971 | B1 | 1/2001 | Doan |
| 6,259,954 | B1 * | 7/2001 | Conger et al. ................ 607/122 |
| 6,374,142 | B1 | 4/2002 | Skinner et al. |
| 6,456,888 | B1 | 9/2002 | Skinner et al. |
| 6,480,747 | B2 | 11/2002 | Schmidt |
| 6,505,401 | B1 | 1/2003 | Doan |
| 6,813,521 | B2 | 11/2004 | Bischoff et al. |
| 6,875,949 | B2 | 4/2005 | Hall |
| 7,158,837 | B2 | 1/2007 | Osypka et al. |
| 7,168,165 | B2 | 1/2007 | Calzada et al. |
| 7,286,882 | B2 | 10/2007 | Cole |
| 7,287,995 | B2 | 10/2007 | Stein et al. |
| 7,292,894 | B2 | 11/2007 | Belden |
| 7,474,924 | B2 | 1/2009 | Honeck et al. |

(Continued)

FOREIGN PATENT DOCUMENTS

| WO | WO0006247 A1 | 2/2000 |
| WO | WO03059439 A2 | 7/2003 |
| WO | WO2007078360 A2 | 7/2007 |
| WO | WO2007089974 A2 | 8/2007 |

*Primary Examiner* — Christopher D Koharski
*Assistant Examiner* — Natasha Patel
(74) *Attorney, Agent, or Firm* — Faegre Baker Daniels LLP (57) ABSTRACT

The embodiments herein relate to a connection body for welding a conductor member to a functional lead component such as a fixation base or terminal pin. The various connection body embodiments each have at least one slot defined in a wall of the connection body at which the conductor member is laser welded to the connection body.

8 Claims, 7 Drawing Sheets

(56) References Cited

U.S. PATENT DOCUMENTS

| | | | |
|---|---|---|---|
| 7,787,961 B1* | 8/2010 | Safarevich et al. | 607/116 |
| 2002/0147488 A1* | 10/2002 | Doan et al. | 607/122 |
| 2002/0193860 A1 | 12/2002 | Bischoff et al. | |
| 2006/0041293 A1 | 2/2006 | Mehdizadeh et al. | |
| 2006/0047223 A1 | 3/2006 | Grandfield et al. | |
| 2007/0038278 A1 | 2/2007 | Zarembo | |
| 2007/0276458 A1 | 11/2007 | Boser | |

* cited by examiner

METHOD AND DEVICES FOR COUPLING A LEAD CONDUCTOR MEMBER TO A FUNCTIONAL COMPONENT

CROSS-REFERENCE TO RELATED APPLICATION

This application claims priority under 35 U.S.C. §119 to U.S. Provisional Application No. 61/181,172, filed on May 26, 2009, entitled "Methods and Devices for Coupling a Lead Conductor Member to a Functional Component," which is incorporated herein by reference in its entirety for all purposes.

TECHNICAL FIELD

The various embodiments disclosed herein relate to body implantable medical devices for sensing electrical impulses and/or delivering electrical stimulation in a body, and more particularly, to a connection body having a slot for coupling a conductor member to a functional component in such devices.

BACKGROUND

Various types of medical electrical leads for use in cardiac rhythm management systems are known. Such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explantation procedures. There is a continuing need for improved lead designs.

SUMMARY

One embodiment disclosed herein relates to a medical lead having a lead body comprising a conductor member connection apparatus. The apparatus includes a connection body operably coupled to the lead body, and a conductor member disposed within the lead body. The connection body includes an opening defined in a first end of the body and a slot defined in a wall of the body. The slot is in communication with the opening and has a length that is parallel to the axis of the lead. The conductor member has a lumen and a first end that is disposed within the opening defined at the first end of the connection body such that at least two filars of the conductor member are visible in the slot. In addition, the two filars are configured to be laser welded to the wall of the body defining the slot. According to one alternative implementation, the apparatus can also have a plug disposed within the lumen at the first end of the conductor member. The plug is configured to be laser welded to the at least two filars of the conductor member and the wall of the body defining the slot.

Another implementation relates to a method of coupling a conductor member to a functional component in a medical lead. The method includes providing a conductor member disposed within a lead body and positioning the conductor member in an opening defined in a first end of the functional component. The first end of the conductor member is positioned adjacent to a slot in a wall of the functional component, wherein the slot is in communication with the opening and has a length that is parallel to the axis of the medical lead. The method further includes welding the conductor member to the functional component along at least half of the length of the slot. In an alternative embodiment, the method also includes positioning a plug in a lumen at the distal end of the conductor member prior to positioning the conductor member in the opening.

Yet another embodiment disclosed herein relates to a medical lead having a lead body with a multilumen tube having a first, continuous lumen, a proximal connector disposed at the proximal end of the lead body, a fixation member disposed on the distal end of the lead body, and a conductor member disposed in the continuous lumen. The proximal connector has a terminal pin disposed at least partially within the proximal connector. The terminal pin has a lumen defined through the terminal pin and at least one pin slot defined in a wall of the pin. The pin slot is in communication with the lumen and has a length that is parallel to the axis of the medical lead. The fixation member has a fixation member base having an opening defined in a proximal end of the base, a base slot defined in a wall of the base, and a fixation helix attached at a distal portion of the base. The base slot is in communication with the opening and has a length that is parallel to the axis of the medical lead. The fixation helix is configured to fix the lead at a site within a patient. The conductor member has a lumen defined through the conductor member, a proximal end disposed through the lumen defined through the terminal pin, a distal end disposed within the opening defined in the proximal end of the base, and a plug disposed within the lumen defined through the conductor member at the distal end of the conductor member. At least two filars of the conductor member are visible through the at least one pin slot and are configured to be welded to the wall of the pin defining the at least one pin slot. In addition, at least two filars of the conductor member are visible through the base slot and configured to be welded to the wall of the base defining the base slot and the plug.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
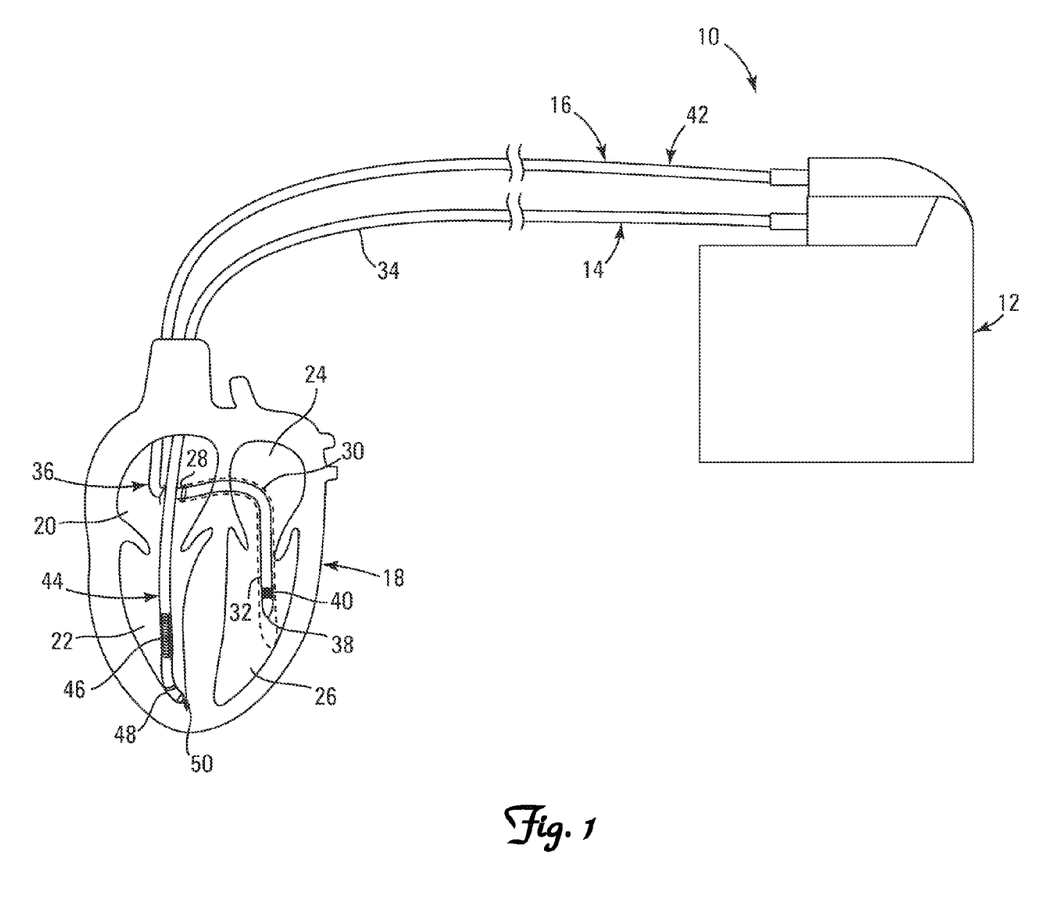
FIG. 1 is a schematic drawing of a cardiac rhythm management system including a pulse generator coupled to a pair of medical electrical leads deployed in a patient's heart, according to one embodiment.

The various embodiments disclosed herein relate to a medical electrical lead having a connection apparatus for coupling a conductor member in the lead to another functional lead component and related methods of making the lead and connection apparatus. The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardioverter defibrillators (ICDs), and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads). FIG. 1 is a schematic drawing of a cardiac rhythm management system 10 including a pulse generator 12 coupled to a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

According to one embodiment, as shown in FIG. 1, lead 14 includes a proximal portion and a distal portion 36, which as shown is guided through the right atrium 20, the coronary sinus ostium 28 and the coronary sinus 30, and into the branch vessel 32 of the coronary sinus 30. The distal portion 36 further includes a distal end 38 and an electrode 40 both positioned within the branch vessel 32. The illustrated position of the lead 14 may be used for delivering a pacing and/or defibrillation stimulus to the left side of the heart 18. Additionally, it will be appreciated that the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 42 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. As will be appreciated, the high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multi-polar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. As will be appreciated, additional electrode configurations can be utilized with the lead 16. In short, any electrode configuration can be employed in the lead 16 without departing from the intended scope of the present invention.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter defibrillator, a cardiac resynchronization (CRT) device configured for bi-ventricular pacing, and/or includes combinations of pacing, CRT, and defibrillation capabilities.

Figure 2:
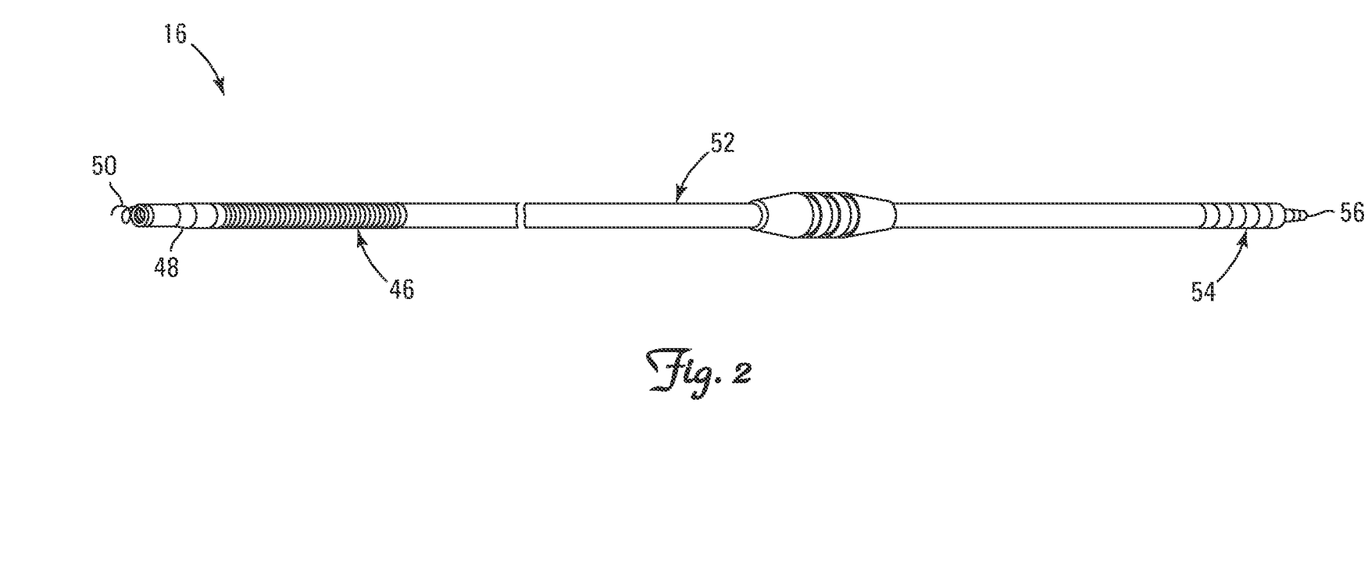
FIG. 2 is a perspective view of one of the leads shown in FIG. 1, according to one embodiment.

FIG. 2 is a perspective view of the lead 16 shown in FIG. 1. As discussed above, the lead 16 is adapted to deliver electrical pulses to stimulate a heart and/or for receiving electrical pulses to monitor the heart. The lead 16 includes an elongated polymeric lead body 52, which may be formed from any polymeric material such as polyurethane, polyamide, polycarbonate, silicone rubber, or any other known polymer for use in this type of lead.

As further shown, the lead 16 further includes a connector 54 operatively associated with the proximal end of the lead body 52. The connector 54 is configured to mechanically and electrically couple the lead 16 to the pulse generator 12 as shown in FIG. 1, and may be of any standard type, size or configuration. The connector 54 has a terminal pin 56 extending proximally from the connector 54. As will be appreciated, the connector 54 is electrically and mechanically connected to the electrodes 46, 48, 50 by way of one or more conducting wires (not shown) within the lead body 52. The conducting wires utilized may take on any configuration providing the necessary functionality. For example, as will be appreciated, the conducting wires coupling the electrodes 48 and/or 50 to the connector 54 (and thus, to the pulse generator 12) may be coiled conductors defining an internal lumen for receiving a stylet or guidewire for lead delivery. Conversely, in various embodiments, the conducting wire to the high voltage electrode 46 may be a multi-strand cable conductor.

According to one embodiment as shown in FIG. 2, the terminal pin 56 has a single electrical contact. Alternatively, the terminal pin 56 has more than one, or two or more, electrical contacts formed thereon.

In some embodiments, the electrode 50 is a fixation helix 50 that is rotatably fixed with respect to the lead body 52. In some such embodiments, the lead body 52 is torquable, allowing the fixation helix 50 to be implanted in body tissue by bringing the fixation helix 50 into contact with body tissue and torquing the lead body 52 to provide torque to the fixation helix 50. As the fixation helix 50 is turned, the helix 50 essentially screws into body tissue at the target location.

In other embodiments, and as will be described in additional detail below, the fixation helix 50 is rotatable with respect to the lead body 52. Further, in some embodiments the terminal pin 56 is rotatable with respect to the proximal connector 54 and the lead body 52. As described in detail below, in some embodiments the terminal pin 56 is connected to the fixation helix 50 such that providing torque to the rotatable portion of the terminal pin 56 imparts a torque on the fixation helix 50, facilitating the implantation of the fixation helix 50 at a desired location. Further, in some embodiments the fixation helix 50 is also provided with a mechanism that facilitates the extension and retraction of the fixation helix 50 from the distal portion of the lead body 52.

Figure 3A:
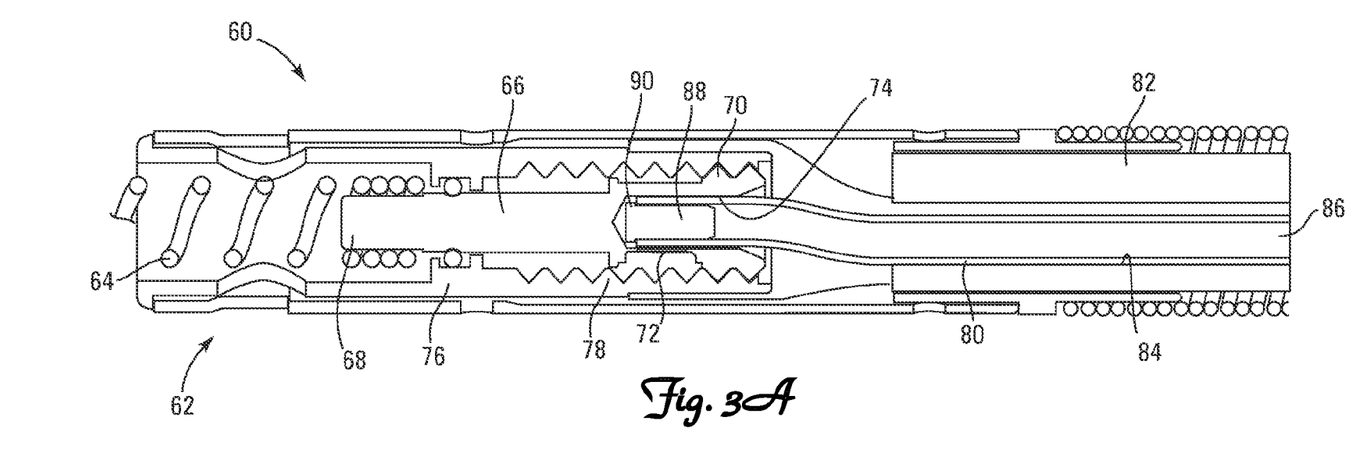
FIG. 3A is a schematic cutaway drawing of a portion of a lead having a connection body with a slot, according to one embodiment.
Figure 3B:
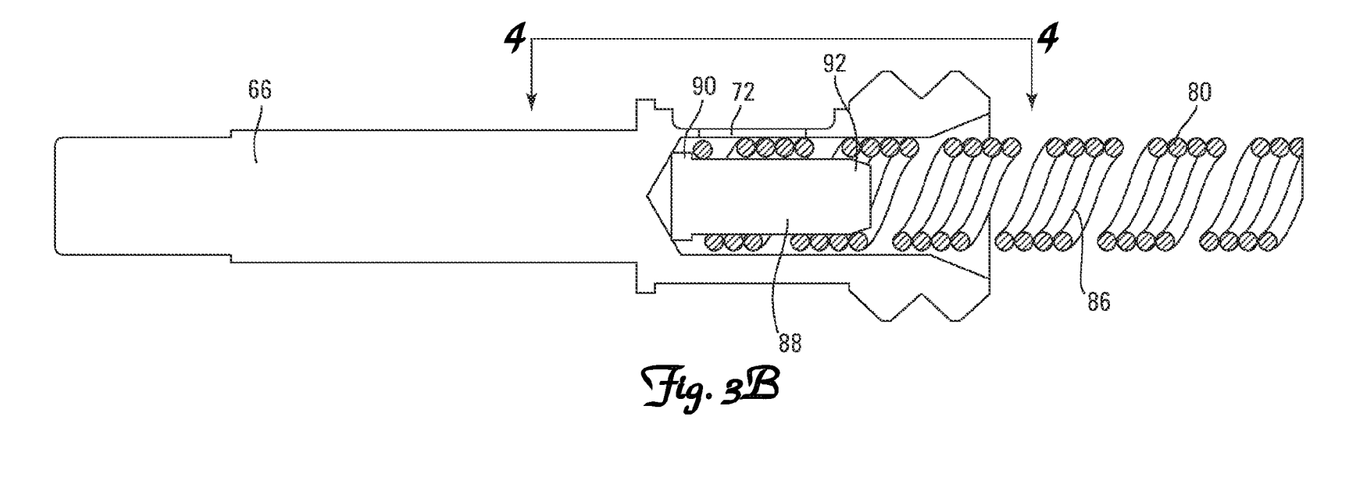
FIG. 3B is an expanded cutaway view of the connection body of FIG. 3A, according to one embodiment.

FIGS. 3A and 3B depict a lead body 60 having a conductor member 80 rotatably disposed therein that is electrically and mechanically coupled to a connection body 66. More specifically, the conductor member 80 and the connection body 66 are positioned as shown in FIGS. 3A and 3B such that the distal end of the conductor member 80 is positioned within the proximal opening 74 of the connection body 66 such that the member 80 and body 66 can be welded together at a slot 72 defined in the connection body 66. Prior to welding, the slot 72 is defined in a wall of the connection body 66 such that the slot 72 is in fluid communication with the proximal opening 74 of the body 66. Note that the connection body 66 as depicted in FIG. 3B is turned 180 degrees on its axis such that the slot 72 is depicted on the top portion of the body 66, while it is depicted on the bottom portion of the body 66 in FIG. 3A.

Figure 4:
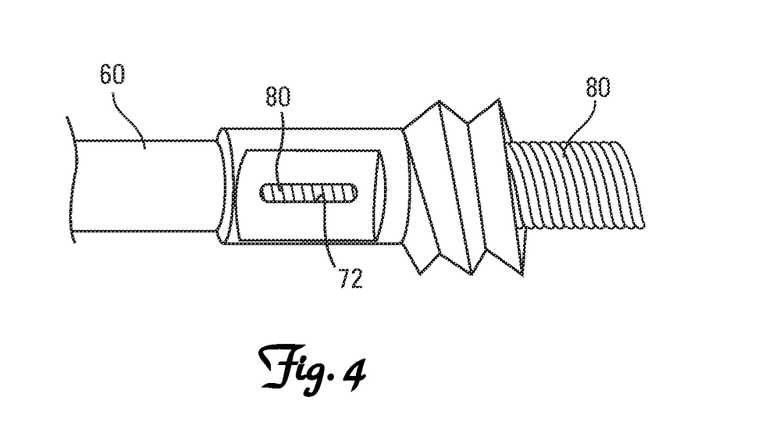
FIG. 4 is an expanded top view of the connection body of FIG. 3B, according to one embodiment.

FIG. 4 is a top view of the connection body 66 embodiment taken along line 4-4 in FIG. 3B. The conductor member 80 has been positioned within the proximal opening (not shown) of the connection body 66 and is thereby visible through the slot 72. As best depicted in this FIG. 4, the slot 72 embodiment in this figure has a length that is parallel to the axis of the connection body 66.

In some embodiments, the presence and the length of the slot 72 provides for visualization and alignment confirmation. That is, the exemplary slot 72 allows the user to look through the slot 72 and visually confirm that the exemplary conductor member 80 is present and positioned correctly within the proximal opening (not shown) of the connection body 66.

Returning to FIG. 3A, the figure shows a longitudinal cross-section of a distal portion 62 of the lead body 60 according to various embodiments. As noted above, the lead body 60 has a fixation helix 64 disposed at the distal portion 62 of the body 60 that is coupled to the connection body 66, which in this embodiment is also referred to as a fixation helix base 66. More specifically, the connection body 66 is disposed within an insert 76 disposed within the distal portion 62 of the lead body 60. The connection body 66 has a seating portion 68 that is also referred to in this embodiment as a fixation helix seating portion 68. In some embodiments such as that shown in FIG. 3A, the seating portion 68 is a reduced dimension portion of the base 66, facilitating the attachment of the fixation helix 64 to the base 66 while still allowing the base 66 to translate axially within the insert 76. Opposite the seating portion 68, the connection body 66 defines a proximal opening 74.

As best depicted in FIG. 3A, the exemplary connection body 66 of this particular embodiment also has first threads 70 formed on an outer surface of the body 66. In addition, second threads 78 are formed on an inner surface of the insert 76. The first and second threads 70, 78 are shaped and configured to mechanically engage one another such that rotating the connection body 66 with respect to the lead body 60 (e.g., with respect to the insert 76), causes the connection body 66 and fixation helix 64 to move longitudinally with respect to the lead body 60 (e.g., with respect to the insert 76). Alternative connection body implementations that provide for extension and retraction of the body for purposes of extending and retracting coupled components (such as, for example, a fixation helix) can have any configuration that facilitates such extension and retraction. Further alternative embodiments in which the connection body does not provide for extension and retraction have no threads or any other configuration to facilitate such movement.

In addition to being coupled to the connection body 66 at a distal portion as discussed above, the conductor member 80 depicted in FIG. 3A is also disposed within and extends through a first lumen 84 defined within the elongate tubular member 82. In the illustrated implementation, the elongate tubular member 82 (also referred to herein as a "multilumen tube") defines at least the first lumen 84 and typically multiple lumens. Alternative embodiments of the elongate tubular member 82 have only a single lumen. The multilumen tube 82 embodiment as shown forms a central or inner portion of the lead body 60 and extends from a proximal portion (not shown) to the distal portion 62 of the body 60. In certain embodiments, the first lumen 84 extends through the tubular member 82 from a proximal end (not shown) to the distal portion 62 of the body 60.

In some embodiments, the conductor member 80 is also a torque transmission member. As discussed in more detail below, in some embodiments the conductor member 80 extends proximally to, and is mechanically coupled to, a rotatable portion of a terminal pin (not shown) positioned at a proximal portion of the lead 60 (similar to the terminal pin 56 depicted in FIG. 2). The conductor member 80 transmits torque from a rotatable portion of the terminal pin (not shown) to the connection body 66. Turning the connection body or fixation helix base 66 within the insert 76 causes the connection body 66 and fixation helix 64 as a whole to simultaneously rotate and move longitudinally, facilitating the implantation of the fixation helix 64. In some embodiments, the conductor member 80 is a coil member and the coil member is elongateable in order to accommodate the longitudinal movement of the connection body 66.

In some such embodiments, the fixation helix 64 is an active fixation helix. For example, electric signals are transmitted between the fixation helix 64 and a portion of the terminal pin (not shown) via the conductor member 80. As such, the contact on the terminal pin (not shown), the conductor member 80, the fixation helix base 66 and the fixation helix 64 are all electrically conductive such that a first electric pathway is formed between the contact (not shown) and the fixation helix 64.

In certain embodiments such as that shown in FIG. 3A, the conductor member 80 defines a lumen 86. In some such embodiments, a stylet (not shown) is provided, and the stylet is sized and configured to be disposed within the lumen 80.

Further, in some embodiments the stylet is torqueable and facilitates the transfer of torque and/or axial force from the terminal pin to the fixation helix 64. In other embodiments, the stylet may impart a shape to the lead 60 and/or the stylet may impart increased stiffness to certain portions of the lead 60.

In certain alternative embodiments, a plug 88 is positioned in the lumen 86 at the distal end of the conductor member 80. As will be described in further detail below, the plug 88 can facilitate the welding process. The plug 88 is positioned such that when the conductor member 80 is correctly positioned within the proximal opening 74 of the connection body 66, the plug 88 is disposed within the lumen 86 adjacent to the portion of the conductor member 80 that is adjacent to the slot 72 and visible through the slot 72. In other words, the plug 88 is positioned adjacent to the portion of the conductor member 80 that is to be welded to the portion of the connection body 66 that defines the slot 72.

In some implementations, the plug 88 has an expanded diameter portion or "lip" 90 at a first end of the plug 88 and a reduced diameter portion or "tip" 92 at a second end. Typically, the lip 90 has a diameter that is greater than the lumen 86 of the conductor member 80. The tip 92 is intended to make insertion into the distal end of the conductor member 80 easier, while the lip 90 is intended to ensure that the plug 88 remains positioned at the distal end of the conductor member 80. Thus, the tip 92 can be inserted into the lumen 86 at the distal end of the conductor member 80, with the reduced diameter of the tip 92 facilitating insertion. When the plug 88 has been fully inserted, the lip 90 contacts the distal end of the conductor member 80 and prevents further insertion of the plug 88.

Alternatively, the plug 88 can be any object having any configuration that can be inserted into the lumen 86 at the distal end of the conductor member 80 for the uses described herein. In one embodiment, the plug 88 is made of a material such as MP35N™, an alloy available from SPS Technologies, Inc. Alternatively, the plug 88 can be made of stainless steel. In a further alternative, it is understood that the plug 88 can be made of any material that is metallurgically compatible with the conductor member 80 and the connection body 66 for purposes of welding.

In other implementations, no plug is used.

Figure 5:
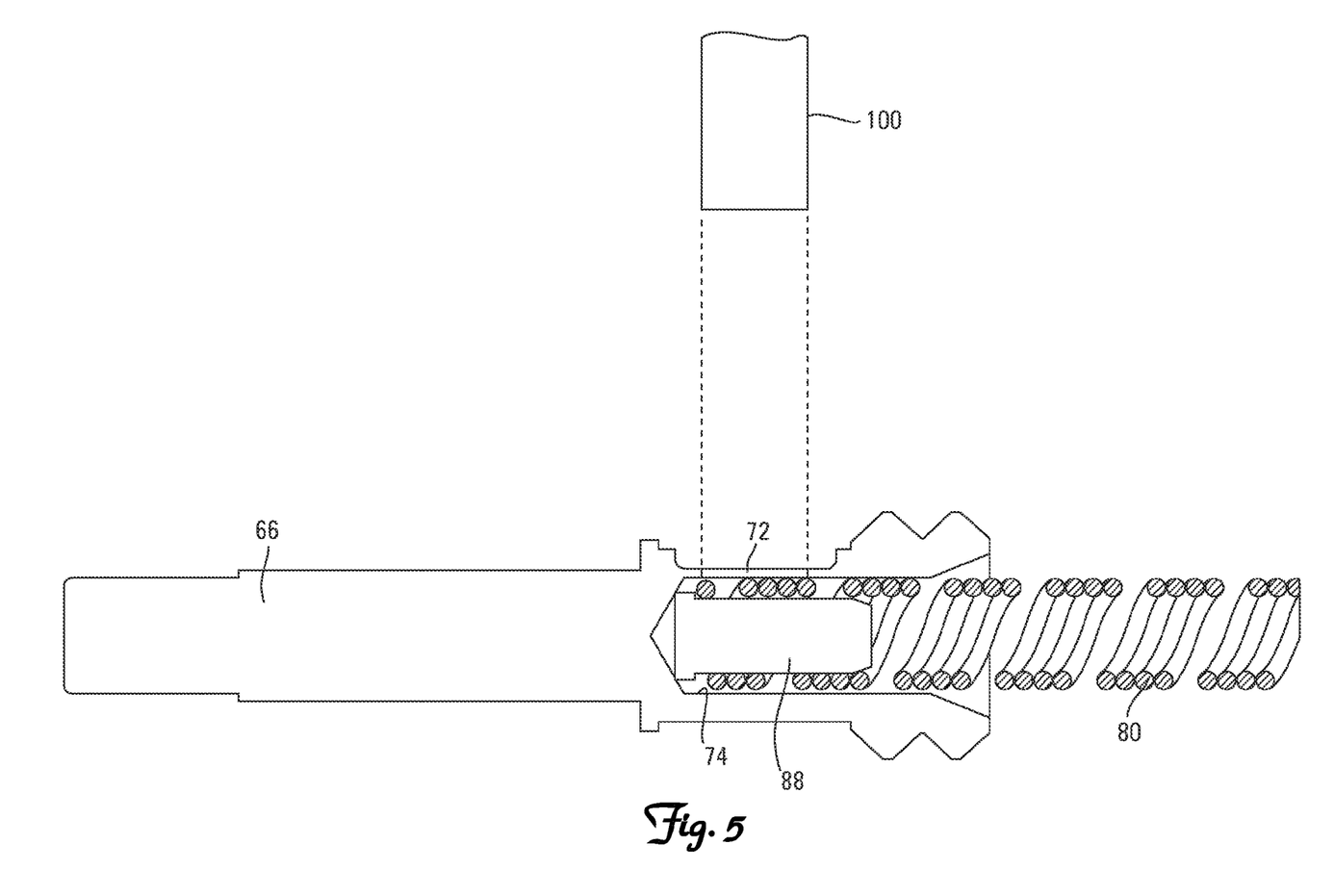
FIG. 5 is a schematic cutaway drawing of a connection body and a laser, according to one embodiment.

One embodiment of a method of coupling a conductor member to a connection body using a laser will now be described. FIG. 5 depicts a laser 100 positioned adjacent to a connection body 66. In this implementation, prior to positioning the connection body 66 and conductor member 80 within the lead (not shown), the distal end of the conductor member 80 is first positioned in the proximal opening 74 as shown in FIG. 5. Then the connection body 66 and a laser 100 are positioned with respect to each other in a configuration similar to that shown in FIG. 5 or in any other configuration such that the laser 100 can be actuated to apply radiation (as shown schematically via the dashed lines) to the material on the connection body 66 defining the slot 72 and the conductor member 80. The application of the laser output welds together the connection body 66 and the conductor member 80 in the area of the slot 72, resulting in a weld mass (not shown) that mechanically and electrically couples the body 66 and member 80.

According to various implementations, one benefit of the slot 72 in the connection body 66 during this welding process is that the user can more reliably confirm the success of the coupling of the body 66 and the conductor member 80. That is, the user can actually see the successful welding together of the two components at the location of the slot 72 and see the resulting weld mass (not shown). Unlike known technologies, this allows the user to confirm with accuracy that the two components have been successfully welded together. The known technologies generally involve a blind, through-penetration welding process in which the user can only see the outer wall of the electrode base and must apply sufficient energy to melt that portion of the electrode base and further to melt the conductor member on the other side of the outer wall of the electrode base while never being able to visually confirm that the two components become coupled as a result of the welding. In contrast, the slot 72 makes it possible to see the welding as it occurs and further makes it possible to apply the laser output directly to the conductor member 80 and the connection body 66. In a further alternative, the slot 72 allows for automated inspection or verification. That is, a vision system as known in the art can be provided that is positioned to automatically verify the presence of a weld mass. In one embodiment, the vision system would provide verification by detecting the absence of the slot 72.

The amount of radiation applied to the slot 72 and conductor member 80 and the length of time of the application is determined by a number of variables, including, but not limited to, the type of connection body 66 material, the conductor member 80 material, the geometry of the slot 72, and the size and dimensions of the connection body 66 and the conductor member 80.

In some embodiments, a plug 88 is positioned at the distal end of the conductor member 80 as shown in FIG. 5. The presence of the plug 88 is another variable that can influence the amount and time period of the laser output. In certain embodiments in which the plug 88 is positioned at the distal end of the conductor member 80 as shown, the plug 88 can create a greater range in the amount of laser radiation or the amount of time that the radiation that is applied to produce a successful weld mass and thus a successful coupling of the body 66 and member 80. More specifically, certain plug 88 embodiments can prevent over-penetration of the weld mass.

To better understand the benefits of the plug, it is informative to understand the welding process without the plug. Without the plug, variation in the welding process and/or in the components can lead to over-penetration of the laser output, which can result in the conductor member being welded to a stylet that might be positioned in the conductor member 80 during the welding process (the stylet is sometimes used to assist in positioning the conductor member 80 in the lead and in the proximal opening 74 of the connection body 66). Over-penetration of the laser output means that too much energy was used or the laser output was applied for too long and too much of the material in the connection body 66 and/or the conductor member 80 (and/or additional components) was melted. The presence of the plug 88 reduces the susceptibility of the connection arrangement to over-penetration by providing an additional material adjacent to the conductor member 80 filars that can be melted into the resulting weld mass, thereby minimizing the chances of melting an additional material that is not intended to be melted into the weld mass.

Thus, the plug 88 allows for the welding together of all three components—the connection body 66 material around the slot 72, the portion of the conductor member 80 adjacent to the slot 72, and the plug 88—while preventing the welding of any additional components. According to one implementation, one example of such a component (one that is not intended to be melted) is a stylet (not shown) disposed within the conductor member 80, as discussed above. The plug 88 absorbs any additional output beyond that required to weld together the connection body 66 and conductor member 80. Thus, the amount of laser radiation applied and the amount of time that it is applied need not be controlled so precisely, thereby allowing a user to apply a greater amount of laser radiation without having to be concerned about applying too much. In addition, the presence of the plug 88 also helps to prevent under-penetration as well. That is, in the absence of a plug, most welding procedures are tuned to apply less energy to avoid the over-penetration described above, thereby increasing the risk of under-penetration. Thus, the presence of the plug 88 means that more energy can be applied, thereby reducing the risk of under-penetration as well. As such, the plug 88 allows the user to use a greater range of laser radiation to couple the connection body 66 and the conductor member 80.

In one specific example such as that shown in FIG. 5 in which a plug 88 is used, the laser radiation applied to the connection body 66 and conductor member 80 at the slot 72 takes the form of multiple pulses of energy ranging from about 500 millijoules ("mJ") to about 610 mJ per pulse. Of course, it is understood that the amount of energy or radiation applied in these various embodiments varies widely depending on the size of the components, the dimensions of the components, and the materials that make up the components. Alternatively, the amount of laser radiation (power and pulses) can be any amount sufficient to weld together the body 66, the conductor member 80 and the plug 88.

Another benefit of the plug 88, according to one embodiment, is that the plug 88 can help to position the conductor member 80. For example, the conductor member 80 depicted in FIG. 5 is a coiled conductor member 80. Without the plug, the filars at the distal end of the coiled conductor member can sometimes bunch up or become misaligned radially as a result of the force applied as the distal end of the conductor member is inserted into the proximal opening 74 of the connection body 66. In contrast, the plug 88 serves to ensure that the filars are aligned radially and can even help to compress the filars axially at the distal end, thereby optimizing the number of filars that are welded to the connection body 66.

In alternative implementations, a plug may not be used. For example, the coupling of a conductor member to another type of functional component (other than a fixation helix) via a connection body might require that the lumen of the conductor member be open to receive components other than a plug. There may also be other reasons that a plug is not used in various configurations.

In one specific embodiment in which a plug is not used, the amount of laser radiation takes the form of multiple pulses ranging from about 130 mJ to about 190 mJ. Of course, as discussed above, the amount of energy or radiation applied in these various embodiments varies widely depending on the various characteristics of the components. Alternatively, the amount of laser radiation (power and pulses) can be any amount sufficient to weld together the body 66 and the conductor member 80. In one further alternative, the amount can be any amount sufficient to weld together the body 66 and the member 80 while not overpenetrating through the conductor member 80 and into any component present within the lumen of the member 80 (such as, for example, a stylet).

In accordance with one alternative implementation, the slot 98 size can be reduced when a plug is not used. More specifically, when a plug is not used, the slot 98 defined in the wall of the body 66 can be narrower than a slot 98 used with a plug. In this embodiment, the narrower slot 98 can help control weld penetration and thus prevent overpenetration.

In one embodiment, the laser 100 is a Lasag™ SLS 200 CL16 Pulsed Nd:YAG Laser. Alternatively, the laser 100 can be any Nd:YAG laser. In a further alternative, the laser can be any known laser for welding two components together in a medical device.

In one embodiment, the connection body 66 can be made of a commercially available alloy made of 90% platinum and 10% iridium. Alternatively, the body 66 can be made of any appropriate biocompatible material. In one implementation, the conductor member 80 can be made of MP35N™. Alternatively, the conductor member 80 can be silver-cored MP35N™. In a further alternative, the conductor member 80 can be stainless steel. In yet another alternative, the conductor member 80 can be made of any known material for use in a conductor member in a medical device.

When a sufficient amount of laser radiation is applied, the connection body 66 material and the conductor member 80 material in the area of the slot weld 72 melts and mixes together and then hardens together as it cools into a weld mass (not shown).

Figure 6A:
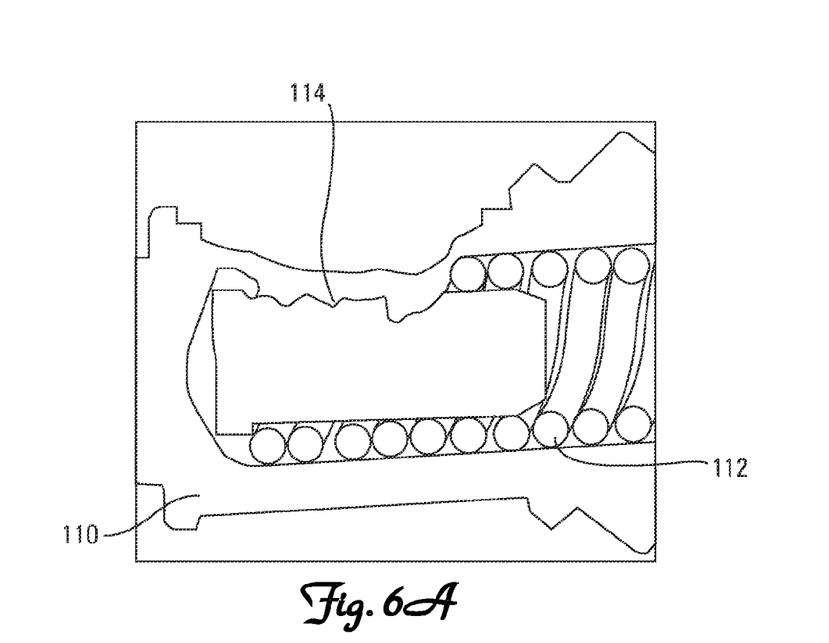
FIG. 6A is schematic cutaway drawing of a connection body with a weld mass, according to one embodiment.
Figure 6B:
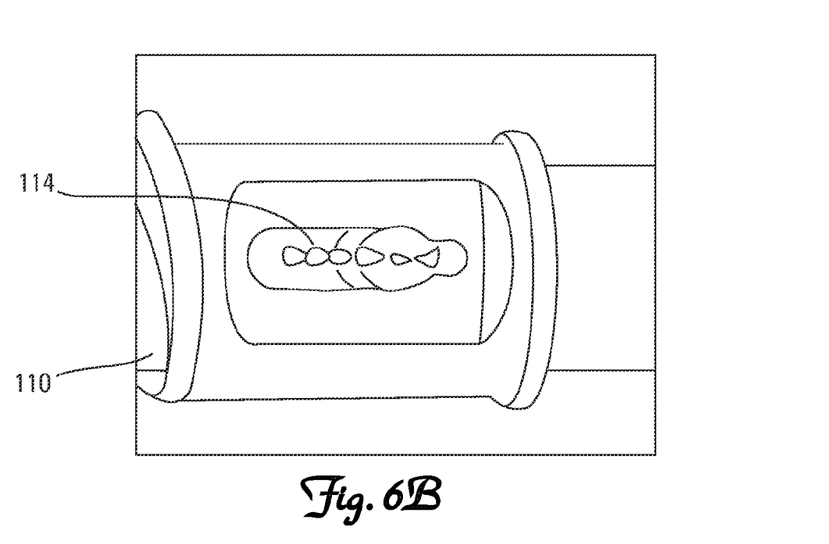
FIG. 6B is a top view of the connection body with the weld mass of FIG. 6A, according to one embodiment.

One example of such a weld mass is shown in FIGS. 6A and 6B, which depict another embodiment of a connection body 110 in which the slot has been welded to the conductor member 112, resulting in a weld mass 114. As described above, the weld mass 114 couples the connection body 110 to the conductor member 112 such that the body 110 and member 112 are coupled mechanically and electrically. More specifically, as best shown in the cutaway view of FIG. 6A, the weld mass 114 is a combination of the connection body 110 material that is adjacent to and defines the slot prior to welding and the material of conductor member 112. As a result of the weld mass 114, the conductor member 112 is mechanically and electrically coupled to the connection body 110 and thus is also electrically coupled to any functional component that is coupled to the connection body 110 (such as, for example, a fixation helix such as that depicted in FIG. 3A).

In accordance with certain implementations, the length of the weld mass 114 as best shown in FIG. 6B (which results from the length of the slot defined in the wall of the connection body 110) is directly related to the strength of the physical coupling of the body 110 and the member 112. That is, the longer the slot (and thus the weld mass 114), the greater the strength of the physical coupling. In addition, in certain embodiments in which the conductor member 112 is a multi-filar conductor, the welding together of all the filars of the multi-filar conductor (as shown in one exemplary embodiment in FIG. 6A) is also directly related to the strength of the physical coupling of the body 110 and member 112. The capturing of all of the filars in the weld mass 114 can be relevant in embodiments such as those described above in which the conductor member 112 is rotatable and torque is applied at a terminal pin (not shown) coupled to a proximal end of the conductor member 112 to cause the conductor member 112 to rotate, thereby causing the connection body 110 to rotate, which in turn causes any functional component attached to the connection body 110 (such as, for example, a fixation helix) to rotate. The greater the force applied to the conductor member 112, the greater the strength of the weld mass 114 (and thus the greater the need to capture all the filars in the weld mass 114) required to ensure that the mass 114 does not break and thus cause a decoupling of the conductor member 112 and the connection body 110.

Figure 7A:
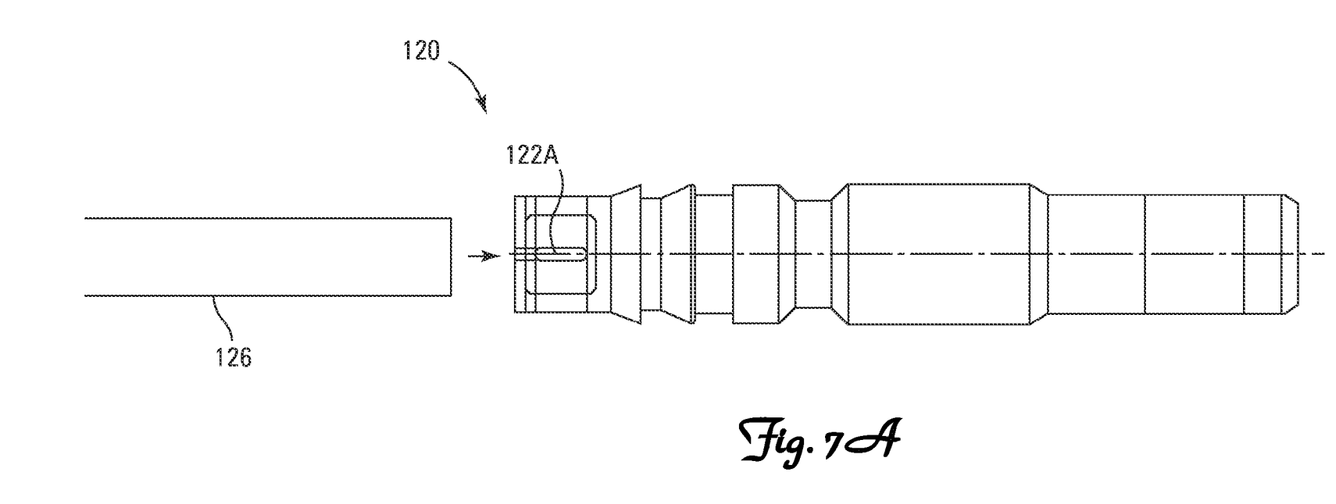
FIG. 7A is a schematic top view of a terminal pin with a first slot, according to one embodiment.
Figure 7B:
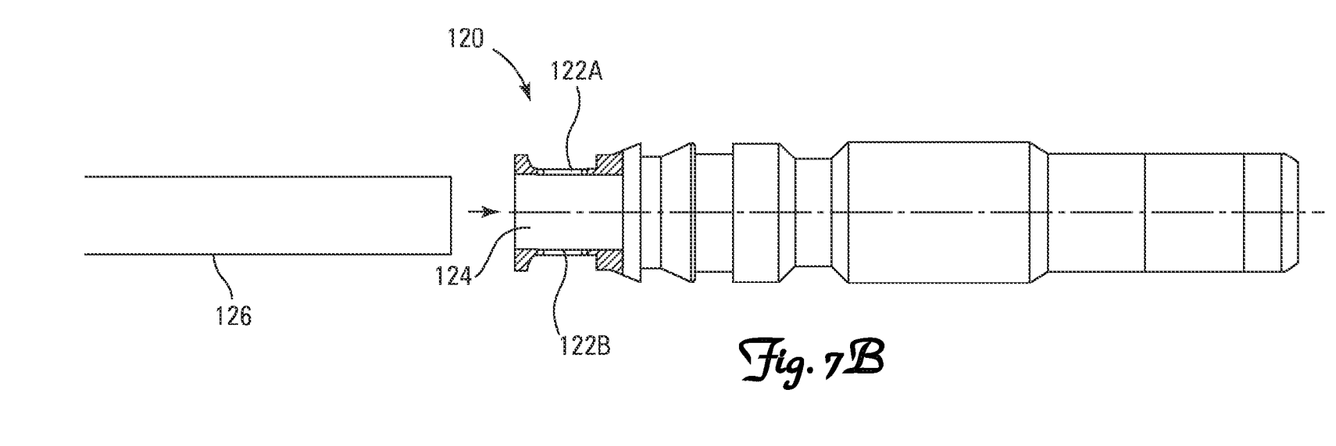
FIG. 7B is a schematic side view of the terminal pin of FIG. 7A, according to one embodiment.

FIGS. 7A and 7B depict an alternative embodiment in which the connection body 120 is a terminal pin 120 (similar in some embodiments to the terminal pin 56 depicted in FIG. 2) that can be welded to the proximal end of a conductor member 126 using two slots 122A, 122B. In this embodiment, as best shown in the top view of the pin 120 in FIG. 7A, the first slot 122A is defined in a wall of the terminal pin 120 at a distal end of the pin 120 with a length that is parallel to the axis of the pin 120. The slot 122A is in communication with the inner lumen 124 that is defined throughout the length of the pin 120. Further, as best shown in the side view of the pin 120 in FIG. 7B, the second slot 122B is defined in the wall of the terminal pin 120 opposite the first slot 122A at the distal end of the pin 120 and is in fluid communication with the inner lumen 124. Similarly, the slot 122B has a length that is parallel to the axis of the pin 120. In various alternative embodiments, the terminal pin 120 can have one slot or more than two slots. In some implementations, two or more slots are helpful—depending on the dimensions of the pin 120 and the slots—to ensure that the conductor member 126 is fully captured in the resulting weld mass. In other implementations, a single slot is sufficient to achieve a sufficient weld mass or to capture all the filars of a multi-filar conductor member.

In this embodiment, the proximal end of the conductor member 126 is inserted into the lumen 124 of the terminal pin 120 at distal end of the pin 120 by moving the conductor member 126 into the lumen 124 in the direction as shown by the arrow such that the proximal end of the conductor member then becomes visible through the slots 122A, 122B. As with the fixation base discussed above, when the conductor member is positioned such that the entire area visible through the slots 122A, 122B is taken up by the proximal end of the conductor member, the conductor member is correctly positioned and can be visually confirmed by a user via the slots 122A, 122B and further can be welded to the terminal pin 120. In this embodiment, the conductor member is welded to the pin 120 at one of the slots and then the other. Alternatively, two lasers can be used to weld the conductor member to the pin 120 at both slots 122A, 122B at the same time.

In accordance with certain implementations, a plug is not used in coupling the conductor member and the pin 120. For example, in some embodiments, it may be desirable to insert a stylet into the lead through the lumen 124 of the terminal pin 120 and into the lumen of the conductor member, and thus the conductor member lumen must be unobstructed and cannot have a plug disposed therein. In alternative embodiments, a plug can be used. In a further alternative, a plug having a lumen therethrough can be used such that a stylet or guidewire can be inserted through the plug.

The laser welding of the conductor member and the terminal pin 120 at the two slots 122A, 122B results in two weld masses that mechanically and electrically couple the conductor member and the pin 120. In addition, according to certain implementations in which the conductor member is a torque transmission member as described above, the strength of the weld masses 122A, 122B allows a user to apply rotational force at the proximal end of the terminal pin 120 that results in torque that is transmitted to the conductor member and thus allows the user to rotate the conductor member within the lead (not shown).

As will be appreciated and as discussed briefly above, connection body and weld mass configurations described herein according to the various embodiments may also be utilized to couple a conductor member to any other functional lead component that needs to be mechanically and/or electrically coupled to the conductor member. It is also understood that the connection body and weld mass configurations discussed above can not only be used with leads for implantation in the coronary venous system, but also leads such as right sided bradycardia or tachycardia leads, right atrial leads, and epicardial leads.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical lead having a lead body, the lead body comprising a conductor member connection apparatus, the connection apparatus comprising:
    a connection body operably coupled with the lead body, the connection body comprising:
    an opening defined in a first end;
    a slot defined in a wall of the connection body, the slot being in communication with the opening, wherein the slot has a length that is parallel to the axis of the medical lead;
    a conductor member disposed within the lead body, the conductor member having a lumen and a first end, wherein the first end of the conductor member is disposed within the opening defined in the first end of the connection body such that at least two filars of the conductor member are visible in the slot for laser welding of the at least two filars to the wall of the connection body defining the slot; and
    a weld mass disposed substantially within the slot joining the at least two filars to the connection body, wherein the weld mass comprises material from the connection body and the at least two filars of the conductor member, and wherein the material from the connection body and the at least two filars are combined as a result of the laser welding.

2. The medical lead of claim 1, further comprising a plug disposed within the lumen at the first end of the conductor member, wherein the plug is configured to be laser welded to the at least two filars of the conductor member and the wall of the body defining the slot.

3. The medical lead of claim 2, wherein the weld mass comprises material from the connection body, the at least two filars of the conductor member, and the plug, wherein the material from the connection body, the at least two filars, and the plug are combined as a result of the laser welding.

4. The medical lead of claim 1, wherein the connection body is a fixation member base, the connection body further comprising:
    a coupling component at a second end of the connection body; and
    a fixation helix coupled to the coupling component.

5. The medical lead of claim 1, wherein the connection body is a terminal pin, the connection body further comprising a proximal pin end at a second end of the connection body.

6. The medical lead of claim 5, wherein the slot is a first slot and the connection body further comprises a second slot defined in the wall of the connection body, wherein the second slot has a length that is parallel to the axis of the medical lead, and further wherein the second slot is positioned opposite the first slot on the wall of the connection body.

7. The medical lead of claim 1, wherein the connection body is associated with a ring electrode.

8. The medical lead of claim 1, wherein the connection body is disposed within and rotatably coupled with the lead body.

* * * * *